United States Patent [19]

Slifkin

[11] Patent Number: 5,508,175
[45] Date of Patent: Apr. 16, 1996

[54] ENVIRONMENTALLY SAFE PARASITOLOGY FIXATIVE AND STAIN

[75] Inventor: Malcolm Slifkin, Pittsburgh, Pa.

[73] Assignee: Allegheny-Singer Research Institute, Pittsburgh, Pa.

[21] Appl. No.: 252,113

[22] Filed: Jun. 1, 1994

[51] Int. Cl.$^6$ .............................. C12Q 1/08; C12Q 3/00; C12Q 1/02
[52] U.S. Cl. .............................. 435/40.5; 435/4; 435/29; 435/40.51
[58] Field of Search ................ 424/7.1, 2, 3; 435/4, 435/29, 40.5, 40.51

[56] References Cited

U.S. PATENT DOCUMENTS

| | | | |
|---|---|---|---|
| 4,666,699 | 5/1987 | Slifkin | 424/7.1 |
| 5,260,048 | 11/1993 | Ryan | 424/3 |

OTHER PUBLICATIONS

Walter B. Wheatley, *A Rapid Staining Procedure For Intestinal Amoebae and Flagellates*, American Journal of Clinical Pathology, vol. 21 (Oct. 1951), pp. 990–991.
Lynne S. Garcia et al., Diagnostic Medical Parasitology, Elsevier Science Publishing Co., (1988), pp. 369–391.
Lynne S. Garcia et al., *Evaluation of Intestinal Protozoan Morphology in Polyvinyl Alcohol Preservative:* ..., Journal of Clinical Microbiology, vol. 31, No. 2 (Feb. 1993), pp. 307–310.
Peter M. Banks, *Technical Aspects of Specimen Preparation and Special Studies,* Surgical Pathology of the Lymph Nodes and Related Organs, Ed. Jaffe, Saunders Publishing Co. (1985) pp. 1–21.
Lennette et al. Manual of Clinical Microbiology Third Edition ASM (1980) pp. 677–687, 1010–1011.
Papamiltiades Cancer Cytology vol. 13, No. 1 (no pages given) 1973.
The Merck Index Merck & Co Ninth Ed (1976) p. 1309.

Primary Examiner—Donald E. Czaja
Assistant Examiner—Jane Williams
Attorney, Agent, or Firm—Webb Ziesenheim Bruening Logsdon Orkin & Hanson

[57] ABSTRACT

A fixative-stain system, which gives superior preservation of nuclear detail, is free from toxic mercury compounds, and which is simple and easy to use, includes a zinc salt and a cobalt salt, in combination, as a fixative, and at least one of Chlorazol Black E, Fast Green FCF and May-Grunwald stains, and preferably the three in admixture, as a staining composition. The fixative may also be used alone. The present fixative-stain system is suitable for fixing and staining all types of parasites such as enteric and other parasites which infect animals and humans.

14 Claims, No Drawings

ENVIRONMENTALLY SAFE PARASITOLOGY FIXATIVE AND STAIN

INTRODUCTION

Many specimens for examination of parasites are collected either at home, in a physician's office, or in a clinic some distance from a laboratory that performs the examination. If timely examination is not possible, portions of specimens are placed into a suitable fixative in order to preserve the delicate diagnostic features of the parasites. To preserve the protozoan morphology and to prevent the continued development of some helminth eggs and larvae, all or a portion of the specimen is placed in fixative either immediately after collection (by the patient using a home collection kit), or once the specimen is received by the laboratory.

Temporary wet-mounts of specimens for direct microscopic examination in the laboratory facilitate the rapid detection of intestinal parasites. The identification of protozoan infections, such as those caused by *Endamoeba histolytica*, can be greatly enhanced by preparing permanent stained smears. The morphology of cysts and trophozoites is better visualized in stained smears that can be used as permanent mounts for future study and for consultation with experts when unusual forms are seen. Permanent stains are prepared as a part of the examination of nearly every specimen submitted for parasitologic examination.

DESCRIPTION OF THE PRIOR ART

Traditional fixatives, namely mercuric chloride or "Schaudinn's fixative", contain mercury as the essential ingredient that promotes preservation of the nuclear detail of various genera of protozoa. Such a preparation is described in "Diagnostic Medical Parasitology" by L. S. Garcia and D. A. Bruckner, published by Elsevier Science Publishing Co., Inc. (1988), "Technical Aspects of Specimen Preparation and Special Studies" by P. M. Banks, and "Evaluation of Intestinal Protozoan Morphology in Polyvinyl Alcohol Preservative: Comparison of Zinc Sulfate- and Mercuric Chloride-Based Compounds for Use in Schaudinn's Fixative" by L. S. Garcia et al. in *J. Clin. Microb.* (February 1993). These mercury-containing fixatives represent a potential biohazard to the environment as well as to the laboratory technician. Various areas, such as Japan and Canada as well as the State of California, have regulations that prohibit the use of mercury-containing reagents, and even in geographic regions as yet unregulated, responsible disposal of mercury-containing wastes is problematic.

Traditional non-mercury-containing fixatives include formalin and sodium acetate-acetic acid-formalin (SAF). Formalin is known to rupture the more delicate protozoa. Although SAF improves the preservation of organism morphology and while both formalin and SAF are absent of mercury, they are "softer" fixatives, i.e. the fixed organisms lack the sharp details obtained with the use of mercuric chloride. Furthermore, formalin is a suspected carcinogen and thus a biohazard in itself.

Mercury salts have been substituted by zinc and copper salts in order to reduce the toxicity of the fixative and to synergistically enhance the fixation process. Organisms have been fixed in zinc sulfate, zinc chloride, copper sulfate, copper chloride, and zinc-formalin, all of which are common and commercially available. These heavy metal fixatives also do not produce the same clarity and morphological detail of organisms as do mercury-containing fixatives.

Accordingly, a need exists for a non-mercury-containing fixative which preserves the nuclear detail of protozoa without damage to the protozoa. It is well established that a fixative can be combined with polyvinyl alcohol (PVA), which acts as an adhesive for the specimen; therefore, a new fixative should also be compatible with PVA. For example, it has traditionally been believed that Chlorazol Black E is a stain incompatible with PVA mounting techniques.

By the terms "fix," "fixed" and "fixative," reference is made to the preservation of the features of the parasites so as to enable diagnostic evaluation. A fixative therefore fixes, or preserves or immobilizes, the various features of the organism such as the nuclear details essential to distinguish one parasite from another. When fixed organisms are applied or adhered to microscope slides or other examination surfaces, such application or adhering is referred to as temporary or permanent mounting. PVA is a polymer of significant utility in mounting fixed organisms for study.

Once a specimen is fixed, and usually after it is mounted, the traditional approach to enhance the visibility of the characteristics of the organism is to stain the organism with a composition which differentially stains it. Typical staining technologies known heretofore include many steps.

The fixed specimen in PVA is first placed on a slide and allowed to air dry, usually 4–6 hours or overnight. At present, the trichrome stain method is widely used in diagnostic laboratories to permit the observation of the presence of parasites in specimens such as stool specimens. Trichrome stain is known as "Wheatley's Trichrome Stain" as described in "A Rapid Staining Procedure for Intestinal Amoebae and Flagellates" by Walter B. Wheatley, Department of Pathology, Lloyd Nolan Hospital, Fairfield, Ala. (1951) and is widely commercially available. This staining method, however, includes many procedural steps including placing the fixed and mounted specimens in different solutions at different times in order to stain any parasites that may be in the specimen. Typically, this entails the following steps: 1) placing the slide into an iodine-alcohol solution for about 20 minutes to remove residual mercury which impedes stain uptake, such step being unnecessary with use of the zinc or copper salt fixatives; 2) placing the slide into a 70% ethanol bath for 5–10 minutes; 3) placing the slide in a second 70% ethanol bath for 5–10 minutes; 4) dipping the slide into trichrome stain for 8 minutes; 5) decolorizing the slide in a phosphotungstic acid bath for a few seconds to wash out excess stain; 6) placing the slide in a 90% ethanol bath for 2 minutes; 7) placing the slide in a second 90% ethanol bath for 2 minutes; 8) placing the slide in a xylene or xylene-phenol bath for 10 minutes or overnight to dry the slide; and 9) adding a mounting material and coverslip to the slide. This staining technique is laborious and lengthy.

Apart from the disadvantages inherent in using typical prior art staining protocols including many and complicated steps, certain stains such as Chlorazol Black E have been identified traditionally as incompatible with PVA or PVA-containing mounting media. Because PVA is a particularly useful mounting medium—it creates no distortion under microscopy, and is water soluble for easy handling—the most useful staining methods and compositions are those which are compatible with PVA.

Therefore, a need remains for a fixative-stain composition system which eliminates the use of mercury to allow easier and more environmentally safe disposal of the reagents, preserves the same level of nuclear detail as do the mercuric fixatives, gives fast and easy staining techniques for wet or permanent mounting without the use of iodine, and allows staining in the presence of PVA.

SUMMARY OF THE INVENTION

The present fixative-stain system, which gives superior preservation of nuclear detail, is free from toxic mercury compounds, and which is simple and easy to use, includes a zinc salt and a cobalt salt, in combination, as a fixative, and at least one of Chlorazol Black E, Fast Green FCF and May-Grunwald stains, and preferably the three in admixture, as a staining composition. The fixative may also be used alone. The present fixative-stain system is suitable for fixing and staining all types of parasites such as enteric and other parasites which infect animals and humans.

DETAILED DESCRIPTION OF THE INVENTION

The present invention is a fixative-stain system, for use in the microscopic identification of protozoa and other parasites, which contains a zinc salt, preferably zinc salicylate, and a cobalt salt, preferably cobalt sulfate, as a fixative combination and a stain composition containing at least one of Chlorazol Black E, Fast Green FCF and May-Grunwald stain, and preferably all three in combination. These compositions are simply contacted onto or into the specimen in which parasite presence is suspected, and any parasites can be examined by ordinary optical microscopy. Each component of the fixative and stain system and its appropriate concentration and parts by volume is described in detail below.

The fixative component of the fixative-stain system contains as its essential ingredients a zinc salt, preferably zinc salicylate, and a cobalt salt, preferably cobalt sulfate. Zinc salicylate in the presence of a cobalt salt has been found, when used as a fixative, to be comparable to mercuric chloride in the preservation of parasite morphology. Cobalt sulfate is the preferred cobalt salt because it solubilizes better than other cobalt salts, e.g. cobalt chloride, however, other cobalt salts are suitable for use with the zinc salt. Zinc salicylate-gives the best preservation of parasite morphology but other zinc salts give roughly comparable results as do traditional mercuric fixatives.

Whereas the essential ingredients of the fixative composition are a zinc salt and a cobalt salt, PVA can be admixed with the zinc salt and the cobalt salt to combine the fixative and a mounting agent in a single composition. As described above, PVA acts as an adherent substance and causes the fixed specimen to adhere to a substrate such as a glass microscope slide. In the preferred embodiment of the present fixative composition, about 4–8% by weight and preferably about 6% by weight is zinc salicylate, about 1–3% by weight and preferably about 2% by weight is cobalt sulfate, about 1–3% by weight and preferably about 2% by weight is acetic acid, about 0.5–2% by weight and preferably about 1% by weight is glycerol, and about 2–6% by weight and preferably about 4% by weight is PVA, all in an about 60–70% aqueous solution of ethanol, preferably an about 50% solution. The acetic acid (or other acetate salt) glycerol and ethanol, while optional, are additional known fixatives which add their own unique preserving abilities to the fixative composition as a whole. These optional constituents do not, however, reproduce the mordant character of mercury as do the present zinc and cobalt salts. A mordant is a histological reagent which attracts and holds any stain thereafter applied, in addition to performing the fixative function.

When it is desirable or convenient to do so, a PVA stock solution may be prepared containing the PVA, glycerol and water. The PVA stock solution can be stored until needed. The PVA stock solution may then be mixed with the acetic acid, the ethanol, the zinc salicylate or other zinc salt, and the cobalt sulfate or other cobalt salt. The resulting fixative solution can be stored at room temperature for anywhere up to several years.

The rapid disintegration of trophozoites is retarded by use of this fixative. A permanent stained specimen completed with the use of a permanent mounting material can be made immediately after fixing or up to three months later. Without immediate fixing of trophozoites, however, reliable diagnostic evaluation is impossible. By the use of the present fixative composition, trophozoites are preserved with excellent resolution but without the use of mercuric fixatives and their concomitant disadvantages.

Specimens including but not limited to feces may be collected, although many of the parasites of interest are enteric parasites and clearly an important diagnostic location of such parasites is in the feces. When fecal specimens are collected for examination, one part feces is generally mixed with three parts of the above-described fixative to yield a specimen ready for examination. Examples of non-fecal specimens are identified as follows, but these are illustrative examples only and are not intended to be limiting.

In sputum, pulmonary amoebiasis and echinococcosis may be detected by examination for trophozoites immediately, with preservation of the trophozites for subsequent staining. Prepared vaginal smears should likewise be placed in the present fixative composition. Anal specimens for *Enterobius vermicularis* should be collected by a tape-slide preparation of a Vaseline- paraffin swab between the hours of 9:00 p.m. and midnight, or in the early morning before defecation or bathing. These parasites may be examined immediately or may, when necessary, be fixed with the present fixative composition. Urine specimens are utilized in the diagnosis of *Trichomonas vaginalis* and *Schistosoma haematobium* infections. The examination of the most fresh urine specimen available, for possible presence of *Trichomonas vaginalis*, should be conducted because the flagella become immobile in older specimens. The optimum urine specimen for *Schistosoma* is collected at, past or shortly after the noon hour, and multiple specimens are recommended. All of these specimens may be fixed in the present fixative composition. Specimens of duodenal secretions examined for *Giardia* trophozoites should be preserved in the present fixative composition unless they can be examined immediately. Specific details and adaptations for implementing the present fixation method with non-fecal specimens are well within the skill of the art.

Ideally, when stool specimens are to be examined, the stool specimen is fixed in a 1:3 ratio with the above-described fixative composition and is allowed to stand for at least 30 minutes at room temperature. Any period of time, however, enhances preservation of morphological detail as compared with the same organisms without fixation. It should be noted that the present fixative composition may be as simple as an aqueous solution containing a zinc salt in combination with a cobalt salt, although the more preferred fixative solutions are described above.

The present fixative compositions, and the method of fixing parasitic organisms which may include separate addition of one or more zinc salts and one or more cobalt salts to a specimen suspected to contain parasites, may be used alone or in conjunction with one or more of the following dyes, admixed in a staining composition. The fixative composition itself may even be admixed to include one or more of the following dyes, although the fixative composition and the stain compositions will usually be kept separate.

Each of the three dyes incorporated into the stain component of the fixative-stain system has a different international color index number and a plurality of synonyms. Chlorazol Black E is also known as C.I. Direct Black 38; Direct deep Black E (FIAT); Pontamine black E, EX, or EXX; Erie black GXOO, B, BF; Direct black MS, RL, E, GX, EE 2V, F or A; Direct deep black EW extra, EA, EAD extra; and Renol black G and has an international color index number of 30235. The chemical formula for Chlorazol Black E is $C_{34}H_{25}N_9O_7S_2Na_2$.

Fast Green FCF has an international color index number of 42053 and its chemical formula is $C_{37}H_{34}N_2O_{10}S_3Na_2$. The synonym for Fast Green FCF is C.I. Food Green 3.

Chromatrope 2R, also known as C.I. Acid Red 29, Chromatrope blue 2R, Chromatrope N2R, Fast Fuchsin G, XL Carmoisine 6R and Acid phloxine OR, which has an international color index of 16570 and chemical formula of $C_{16}H_{10}N_2O_8S_2Na_2$, may be substituted for Fast Green FCF. Light Green SF, also known as C.I. Acid Green 5, and Acid Green L Extra which has an international color index of 42095 and chemical formula of $C_{37}H_{34}N_2O_9S_3Na_2$, may also be substituted for Fast Green FCF.

May-Grunwald stain is a methylene blue eosinate and is also known as Jenner's stain.

Each of the three dyes are commercially available. May-Grunwald is available as a stock solution, and it is sometimes more convenient to store Chlorazol Black E and Fast Green FCF as stock solutions as well. Accordingly, for the purposes of the present application, Stock Chlorazol Black E refers to a solution of about 1–3% by weight, preferably about 2% by weight, Chlorazol Black E in distilled water. Similarly, Stock Fast Green FCF refers to an about 0.3–1% by weight solution of Fast Green FCF, preferably about 0.5% by weight, in distilled water. The stock solutions may be stored at room temperature for several years, if necessary.

In the formulation of a stain composition for use in the present stain-fixative system, one or more dyes are admixed in solution in amounts which yield superior resolution of the diagnostic characteristics of the parasites. In the preferred embodiment of the present stain composition, the following are present: about 10–18% by weight of Stock Chlorazol Black E dye, preferably about 14% by weight, about 10–18% by weight is Stock Fast Green FCF, preferably about 14% by weight, and about 64–80% by weight, preferably about 72% by weight, is May-Grunwald stain. However, any one or more of these dyes may be present in a stain composition particularly suited for use .in conjunction with the above-described fixative composition.

Suitable microscope slides include wet mount slides and permanent smears. Wet mount slides and permanent smears are very similar microscope slides, differing only in that the permanent smear has been treated to create a permanent mount. The wet mount, however, also offers a beneficial degree of preservation: a wet mount slide prepared directly from the fixed, optionally stained specimen described above will not deteriorate for at least 48 hours after its preservation, providing more than adequate specimen preservation for even the busiest of laboratories.

To prepare a permanent mount, a sample of the fixed specimen is placed into a test tube to which an aliquot of the stain composition is added. The tube is capped and incubated for at least about 60 minutes at room temperature to allow the stain to penetrate any protozoa in the specimen. Incubation with the stain may proceed for 12 to 18 hours. The fixed and stained specimen is remixed. Using an applicator stick, a few drops of the fixed and stained specimen is spread across the bottom third of a microscopic slide to create a thin smear. The slide is placed, typically, in an absolute ethanol alcohol bath for 1 minute. The slide is then placed in a second absolute alcohol bath for 1 minute. The slide is then placed in xylene for 3 minutes or overnight. Finally, the fixed and stained sample thus mounted is permanently mounted in "Permount" or similar mounting medium, and covered with a coverslip. The specimen is examined under optical microscopy using both low and high power and, as necessary, the oil-immersion technique.

To prepare a wet-mount smear the stool or other specimen should be allowed to fix for at least 30 minutes at room temperature, in admixture with about three times its weight in fixative composition. A sample of the fixed specimen is placed into a test tube to which an aliquot of the desired stain composition is added. The stained and fixed specimen are mixed well and capped and incubated about 60 minutes at room temperature to allow the stains to penetrate any protozoa in the fecal specimen. Incubation with the stain may proceed for 12 to 18 hours. The fixed and stained specimen is remixed. A thin drop of the fixed and stained specimen is placed on a microscope slide and covered with a microscope coverslip. The specimen should be examined under low power with low light intensity, making certain to examine the entire specimen. Suspect objects may be examined under high power, with dry and/or oil immersion techniques.

When a stain composition containing all three dyes is used, the nuclei of parasites stain blue-to-blue-black; the cytoplasm of parasites is pink-to-red to various shades of light purple; and karyosomes, flagella and axonemes stain blue-to-blue-black.

The invention will be more fully described with reference to the specific examples herein set forth. It should be noted that the diagnostic results obtained with the present method are identical with the results obtainable with Wheatley's Trichrome Stain, which contains mercury.

EXAMPLE 1

A basic fixative composition was prepared by first mixing 60 grams zinc salicylate in 500 ml absolute ethanol. 500 ml of PVA stock solution was added and mixed well to remove precipitates. Twenty grams of cobalt sulfate dissolved in 32 ml distilled water and 20 ml glacial acetic acid were subsequently added. The solids were allowed to dissolve in the PVA stock solution under mixing. Addition of the absolute ethanol was followed by mixing to remove precipitate that forms when the ethanol comes in contact with the PVA.

The PVA stock solution was prepared by mixing 20 grams PVA with 6.0 ml glycerol and 250 ml distilled water. The PVA stock solution was mixed and then heated to 80° C. for a few minutes, shaking frequently. The solution was then remixed, cooled and stored at room temperature.

EXAMPLE 2

Fixed fecal specimens were prepared by filling vials with 15 ml of fixative of Example I and capping the vials with a collection spoon and were then stored at room temperature. About 3 spoonfuls of hard formed stool or 5 spoonfuls of soft stools were added to each vial and thoroughly mixed with the fixative composition according to Example 1, using the spatula. The cap was replaced and each vial was shaken until the specimen was well mixed. The fixed specimen was allowed to stand for at least 30 minutes.

EXAMPLE 3

A basic stain composition was prepared containing 2.0 ml of stock Chlorazol Black E aqueous solution, 2.0 ml of a stock Fast Green FCF aqueous solution and 10 ml of May-Grunwald stain composition. The stain was mixed and then centrifuged to remove precipitate associated with Chlorazol Black E. The resultant stain component was stored at room temperature.

The stock Chlorazol Black E solution was prepared by adding 2 grams Chlorazol Black E to a glass container to which 100 ml distilled water was added and capped lightly. The container was microwaved 5 times for 10 seconds each and cooled. Heating systems other than microwave heating may be used to solubilize the dye. The stock Chlorazol Black E solution was stored at room temperature.

The stock Fast Green FCF solution was prepared by adding 0.5 grams Fast Green FCF to 100 ml distilled water. The solution was mixed to dissolve the stain and stored at room temperature.

EXAMPLE 4

A fixed and stained specimen was prepared by placing 1 ml of the fixed specimen in a test tube to which 25 drops (about 0.25 ml) of the stain composition Example 3 was added and mixed. The test tube was capped and incubated at room temperature for 60 minutes to allow the stain to penetrate any protozoa in the fecal specimen. The specimen was then remixed.

EXAMPLE 5

A permanent stained smear was prepared by remixing the fixed and stained specimen of Example 4. A few drops of the specimen of Example 4 was applied to the bottom third of a microscope slide with an applicator stick and spread thinly across the slide to create a thin smear. The microscope slide was placed in absolute ethanol for 1 minute and a second application of ethyl alcohol for a second minute, followed by a xylene bath for 3 minutes. The slide was mounted in Permount, covered with a coverslip and examined with optical microscopy.

EXAMPLE 6

A wet mount was prepared by remixing the fixed and stained specimen prepared in accordance with Example 4. One drop of the fixed and stained specimen was placed on a microscope slide. A coverslip was placed over the drop of fixed stained specimen. The slide was examined under low power (10X) low light intensity. Suspect objects were examined with high dry and oil immersion.

What is claimed is:

1. A method of fixing and staining a specimen suspected to contain parasites, comprising:
   preparing a fixative composition by admixing at least one zinc salt and at least one cobalt salt in solution;
   mixing a specimen with an aliquot of said fixative composition; and
   adding to said specimen at least one dye selected from the group consisting of Chlorazol Black E, Fast Green FCF and May-Grunwald stain.

2. The method of claim 1 wherein said fixative composition further comprises an about 60–70% aqueous ethanol solution containing about 4–8% by weight of zinc salicylate, about 1–3% by weight of cobalt salt, about 1–3% by weight of acetic acid, about 0.5–2% by weight of glycerol and about 2–6% by weight of polyvinyl alcohol.

3. The method of claim 1 wherein said at least one dye is present in a stain composition, wherein said Chlorazol Black E is in aqueous solution and is present in said stain composition in the amount of about 10–18% by weight of an about 1–3 weight % aqueous solution of Chlorazol Black E, wherein said Fast Green FCF is in aqueous solution and is present in said stain composition in the amount of about 10–18% by weight of an about 0.3–1% by weight aqueous solution of Fast Green FCF, and wherein said May-Grunwald Stain is in aqueous solution and is present in said stain composition in the amount of about 64–80% by weight.

4. The method of claim 1 wherein said specimen is a fecal specimen and further wherein one part fecal specimen is admixed with about three parts of said fixative composition.

5. The method of claim 1 wherein said fixative composition is an about 50% aqueous ethanol solution containing about 6% by weight of zinc salicylate, about 2% by weight of said cobalt salt, about 2% by weight acetic acid, about 1% by weight glycerol and about 4% by weight of polyvinyl alcohol.

6. A method of fixing and staining a fecal specimen for microscopic viewing comprising:
   preparing a fixative composition by combining an aqueous solution of ethanol with zinc salicylate, a cobalt salt, acetic acid, glycerol, and polyvinyl alcohol;
   preparing a specimen mixture comprising fecal matter and a portion of said fixative composition;
   preparing a stain composition by combining in solution at least one solution selected from the group consisting of an aqueous solution of Chlorazol Black E Stain, an aqueous solution of Fast Green FCF and May-Grunwald stain;
   preparing a stained specimen mixture comprising an aliquot of said specimen mixture with an aliquot of said stain composition; and
   mounting an aliquot of the resulting admixture for examination.

7. The method of claim 6 wherein said fixative composition is an about 60–70% aqueous ethanol solution containing about 4–8% by weight of said zinc salicylate, about 1–3% by weight of said cobalt salt, about 1–3 volume % of said acetic acid, about 0.5–2% by weight of said glycerol and about 2–6% by weight of said polyvinyl alcohol.

8. The method of claim 6 wherein said aqueous solution of Chlorazol Black E is about 10–18% by weight of said stain composition of an about 1–3% by weight aqueous solution of Chlorazol Black E, said aqueous solution of Fast Green FCF is about 10–18% by weight of said stain composition of an about 0.3–1% by weight aqueous solution of Fast Green FCF and said May-Grunwald Stain is about 64–80% by weight of said stain composition.

9. The method of claim 8 wherein said fixative composition is an about 50% aqueous ethanol solution containing about 6% by weight of said zinc salicylate, about 2% by weight of said cobalt salt, about 2% by weight of said acetic acid, about 1% by weight of said glycerol and about 4% by weight of said polyvinyl alcohol.

10. The method of claim 9 wherein said aqueous solution of Chlorazol Black E is about 14% by weight of said stain composition of an about 2% by weight aqueous solution of Chlorazol Black E, said aqueous solution of Fast Green FCF is about 14% by weight of said stain composition of an about 0.5% by weight aqueous solution of Fast Green FCF and said May-Grunwald Stain is about 72% by weight of said stain composition.

11. The method of claim 10 comprising the additional steps of:

spreading a thin layer of a few drops of said resulting admixture across a microscope slide;

placing said slide in a first absolute ethyl alcohol bath for 1 minute;

placing said slide in a second absolute ethyl alcohol bath for 1 minute;

placing said slide in a xylene bath for 3 minutes to overnight;

mounting said slide in a mounting medium; and viewing said slide with oil immersion.

12. The method of claim 11, comprising the additional steps of:

placing a coverslip over said thin layer; and viewing said slide under optical microscopy.

13. A method for fixing a specimen suspected to contain parasites, comprising adding to said specimen at least one zinc salt and at least one cobalt salt, to fix said specimen.

14. A method for fixing a specimen suspected to contain parasites, comprising adding to said specimen an aqueous solution of zinc salicylate and adding to said specimen an aqueous solution of cobalt sulfate, to fix said specimen.

* * * * *